United States Patent [19]

Chang

[11] Patent Number: 5,738,099
[45] Date of Patent: Apr. 14, 1998

[54] PORTABLE ULTRASONIC DIAGNOSTIC APPARATUS

[75] Inventor: Seong Ho Chang, Seoul, Rep. of Korea

[73] Assignee: Medison Co., Ltd., Kangwon-do, Rep. of Korea

[21] Appl. No.: 712,295

[22] Filed: Sep. 11, 1996

[30] Foreign Application Priority Data

Sep. 13, 1995 [KR] Rep. of Korea .................. 95-29912

[51] Int. Cl.⁶ ............................................. A61B 8/00
[52] U.S. Cl. ............................................. 128/662.03
[58] Field of Search .................. 128/660.04, 660.05, 128/660.07, 660.1, 662.03; 73/620

[56] References Cited

U.S. PATENT DOCUMENTS

| 3,964,296 | 6/1976 | Matzuk | 128/660.1 |
| 4,246,792 | 1/1981 | Matzuk | 73/620 |

*Primary Examiner*—George Manuel
*Attorney, Agent, or Firm*—Morgan & Finnegan, L.L.P.

[57] ABSTRACT

A portable ultrasonic diagnostic apparatus comprising a pistol-shaped housing. A liquid crystal display (LCD) for displaying a result of ultrasonic diagnosis is installed in a portion of the pistol-shaped housing and a single element probe is installed in the muzzle portion of the pistol-shaped housing for use as a probe.

7 Claims, 1 Drawing Sheet

/ 1

PORTABLE ULTRASONIC DIAGNOSTIC APPARATUS

BACKGROUND OF INVENTION

1. Field of the Invention

The present invention relates to a portable ultrasonic diagnostic apparatus, and more particularly, to a pistol-shaped portable diagnostic apparatus.

2. Description of the Prior Art

An ultrasonic diagnostic apparatus scans an ultrasonic wave to a human body and converts information loaded on a reflected ultrasonic wave into an electrical signal using a piezoelectric effect of a probe, to thereby display the electrical signal on a screen. Therefore, the ultrasonic diagnostic apparatus can enable a user to obtain information of the inside of a human body, without cutting out the affected parts of the human body.

However, conventional ultrasonic diagnostic apparatuses have the undesirable characteristic of being bulky and heavy. Even a compact model weighs more than 10 Kg, which makes it difficult to move and impossible to carry.

SUMMARY OF THE INVENTION

To solve the above-mentioned problem, it is an object of the present invention to provide a portable ultrasonic diagnostic apparatus.

To accomplish this and other objects of the present invention, there is provided a portable ultrasonic diagnostic apparatus that comprises a pistol-shaped case or housing. A liquid crystal display (LCD) is installed in a portion of the pistol-shaped case and is used for displaying a result of ultrasonic diagnosis. A single element probe is installed in the muzzle portion of the pistol-shaped case for use as a probe.

The foregoing specific object and advantages of the invention are illustrative of those which can be achieved by the present invention and is not intended to be exhaustive or limiting of the possible advantages which can be realized. Thus, this and other objects and advantages of this invention will be apparent from the description herein or can be learned from practicing this invention, both as embodied herein or as modified in view of any variations which may be apparent to those skilled in the art. Accordingly, the present invention resides in the novel parts, constructions, arrangements, combinations and improvements herein shown and described.

BRIEF DESCRIPTION OF THE DRAWINGS

The above object and advantages of the present invention will become more apparent by describing in detail preferred embodiments thereof with reference to the drawings in which.

DETAILED DESCRIPTION OF THE INVENTION

Figure 1:
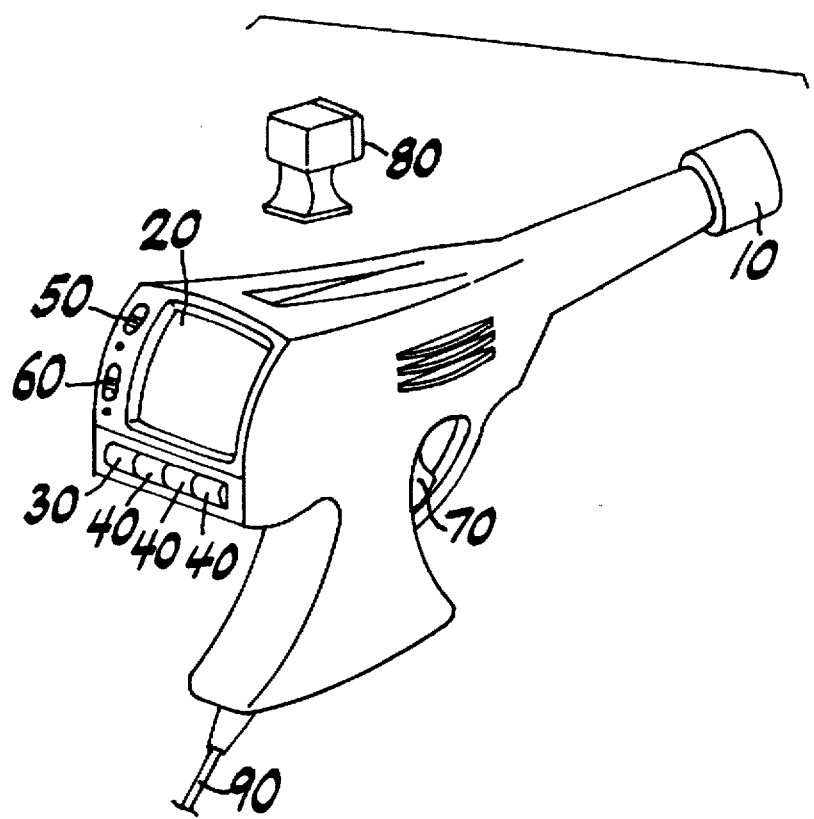
FIG. 1 is a schematic view of a portable ultrasonic apparatus according to the present invention.

A preferred embodiment of the present invention will be described below in detail with reference to the accompanying drawings.

A probe 10 scans an ultrasonic wave and converts a reflected ultrasonic wave into an electrical signal. It is preferable that a single element probe be used as the probe in order to minimize the volume and weight of the ultrasonic diagnostic apparatus.

An electronic circuit for processing an analog signal and a digital signal to perform ultrasonic diagnosis is installed in the body of the pistol-shaped ultrasonic diagnostic apparatus. A display 20 displays an ultrasonic diagnosis result of which the signal has been processed on a screen. It is preferable that such a display be an LCD display. Since the LCD display has a small and thin screen, it is appropriate for a portable ultrasonic diagnostic apparatus. A user can adjust the brightness of the screen on which the image is displayed using a brightness control key 50. Also, the user can adjust the contrast of shape of the displayed image using a contrast control key 60.

Power for operating the ultrasonic diagnostic apparatus is supplied via a power cable 90 or using a battery such as a dry cell. The user operates the portable ultrasonic diagnostic apparatus by depressing a power key 30. A function select key 40 enables the user to select various functions of the ultrasonic diagnostic apparatus. The portable ultrasonic diagnostic apparatus according to the present invention can include a picture stop function as an auxiliary function. That is, using a freeze key 70, a particularly displayed picture can be changed into a picture which is being actually scanned. Also, the portable ultrasonic diagnostic apparatus according to the present invention includes a detachable lamp 80 to enable the user to facilitate diagnosis in a dark place.

As described above, the portable ultrasonic diagnostic apparatus according to the present invention includes an LCD display for displaying the result of the ultrasonic diagnosis and a single element probe as a probe in a pistol-shaped case or housing, thereby minimizing the volume and the weight of the ultrasonic diagnostic apparatus and providing a convenient use.

Although an illustrative preferred embodiment has been described herein in detail, it should be noted and will be appreciated by those skilled in the art that numerous variations may be made within the scope of this invention without departing from the principle of this invention and without sacrificing its chief advantages. The terms and expressions have been used as terms of description and not terms of limitation. There is no intention to use the terms or expressions to exclude any equivalents of features shown and described or portions thereof and this invention should be defined in accordance with the claims which follow.

What is claimed:

1. A portable ultrasonic diagnostic apparatus, comprising:

a pistol-shaped housing;

a probe positioned in a muzzle of the pistol-shaped housing;

an electronic circuit installed in the housing, the circuit capable of converting a frequency signal supplied from the probe into a video signal to be displayed;

a liquid crystal display (LCD) installed in a portion of the housing opposite the probe, the display capable of displaying the video signal supplied by the electronic circuit;

a brightness control key installed in a portion of the housing to enable a user to adjust the brightness of an image displayed on the LCD;

a contrast control key installed in a portion of the housing to enable a user to adjust the contrast of shape of the image displayed on the LCD; and a user manipulation keypad installed in a portion of the housing to enable a user to operate or select various functions of the ultrasonic diagnostic apparatus.

2. The portable ultrasonic diagnostic apparatus according to claim 1, wherein the probe is a single element probe.

3. The portable ultrasonic diagnostic apparatus according to claim 1, further comprising a freeze key for selecting a function of stopping a particularly displayed picture and changing the stopped picture into an actually scanned picture, the freeze key being located on the housing in a position to enable convenient operation by the user.

4. The portable ultrasonic diagnostic apparatus according to claim 3, further comprising a lamp for facilitating a diagnosis in a dark place.

5. The portable ultrasonic diagnostic apparatus according to claim 4, wherein the lamp is detachable from the pistol-shaped housing.

6. The portable ultrasonic diagnostic apparatus according to claim 3, wherein the freeze key is located as a trigger on a handle portion of the pistol-shaped housing.

7. The portable ultrasonic diagnostic apparatus according to claim 1, further comprising a lamp for facilitating a diagnosis in a dark place.

* * * * *